US006524614B2

(12) United States Patent
Cannell et al.

(10) Patent No.: US 6,524,614 B2
(45) Date of Patent: *Feb. 25, 2003

(54) COMPOSITIONS AND METHODS FOR CONTROLLING DEPOSITION OF WATER-INSOLUBLE INGREDIENTS

(75) Inventors: David W. Cannell, New York, NY (US); Nghi Nguyen, Edison, NY (US); Hitendra Mathur, Woodbridge, NJ (US); Cynthia Espino, Princeton, NJ (US)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/934,488

(22) Filed: Aug. 23, 2001

(65) Prior Publication Data

US 2002/0009425 A1 Jan. 24, 2002

Related U.S. Application Data

(63) Continuation-in-part of application No. 09/205,692, filed on Dec. 4, 1998, now abandoned.

(51) Int. Cl.$^7$ ............................. A61R 9/127; A61R 7/00
(52) U.S. Cl. ..................... 424/450; 424/401; 424/70.1; 424/70.2; 424/70.11; 424/70.21; 424/70.22; 424/73; 514/881; 514/937
(58) Field of Search ................................ 424/401, 450, 424/40.1, 70.2, 70.11, 70.21, 70.22, 73; 514/881, 934

(56) References Cited

U.S. PATENT DOCUMENTS

| 3,996,146 A | 12/1976 | Tarasov et al. |
| 4,174,296 A | 11/1979 | Kass |
| 4,832,872 A | 5/1989 | Scandel |
| 4,874,553 A | 10/1989 | Hager et al. |
| 5,002,761 A | 3/1991 | Mueller et al. |
| 5,160,739 A | 11/1992 | Kanga ........................ 424/401 |
| 5,173,303 A | 12/1992 | Lau et al. |
| 5,783,554 A | 7/1998 | Li ............................. 510/488 |
| 5,804,203 A | 9/1998 | Hahn ......................... 424/401 |
| 6,015,574 A | 1/2000 | Cannell et al. |

FOREIGN PATENT DOCUMENTS

| BE | 895 719 A1 | 7/1983 |
| EP | 123 071 | 10/1984 |
| EP | 340 592 | 11/1989 |
| EP | 0 521 799 A1 | 1/1993 |
| EP | 0 868 898 A1 | 7/1998 |
| EP | 0 872 229 A1 | 10/1998 |
| WO | WO 98/56333 | 12/1998 |

OTHER PUBLICATIONS

Copy of co-pending application No. 09/207,656.
Copy of co-pending application No. 09/328,785
Copy of co-pending application No. 09/328,384.
Ribosa et al., "Physico-chemical Modifications of Liposome Structures Through Interaction With Surfactants," *International Journal of Cosmetic Science*, pp. 131–419 (1992).
English Language Abstract of BE 895 719 A1.
International Search Report, dated Apr. 14, 2000.

*Primary Examiner*—Gollamudi S. Kishore
(74) *Attorney, Agent, or Firm*—Finnegan, Henderson, Farabow, Garrett & Dunner, L.L.P.

(57) ABSTRACT

A composition useful in a delivery system for water-insoluble ingredient(s) containing at least one organic phospholipid capable of forming bilayers in aqueous solution; at least one amphoteric surfactant present in an amount by weight equal to or greater than the amount of the phospholipid; at least one nonionic surfactant present in an amount by weight equal to or greater than the amount of the phospholipid; and at least one cationic polymer, wherein the cationic polymer functions to control the amount of water-insoluble ingredient(s) deposited on keratinous substances. A method for treating keratinous substances with the compositions and delivery systems is also disclosed. In addition, the amount of water-insoluble ingredient(s) to be deposited can be controlled by varying the amount of the phospholipid, the nonionic surfactant, or both.

50 Claims, No Drawings

US 6,524,614 B2

COMPOSITIONS AND METHODS FOR CONTROLLING DEPOSITION OF WATER-INSOLUBLE INGREDIENTS

This is a continuation of application Ser. No. 09/205,692, filed Dec. 4, 1998 now abandoned, which is incorporated herein by reference.

FIELD OF THE INVENTION

The present invention relates to compositions and delivery systems based on a combination of organic phospholipids capable of forming bilayers in aqueous solution; amphoteric surfactants; nonionic surfactants; and cationic polymers, wherein the combination of these ingredients allows water-insoluble ingredients to be incorporated into aqueous solutions. The deposition of the water-insoluble ingredients on the keratinous substances can be controlled by varying the amounts of certain of the above components.

BACKGROUND OF THE INVENTION

Organic phospholipids play an important role in the cosmetics and pharmaceutical industries because of their outstanding physiological properties, such as, for example, emulsifying, softening, and anti-oxidant effects. When hydrolyzed, organic phospholipids yield phosphoric acid, an alcohol, a fatty acid, and a nitrogenous base. Most phospholipids are amphipathic, i.e., have polar "heads" and non-polar "tails." As a result, most phospholipids tend to arrange spontaneously into a bilayer when suspended in an aqueous environment, with the polar heads contacting the water and the non-polar tails contacting each other. Most naturally occurring phospholipids prefer to form vesicular bilayers in water solutions. In such a bilayer vesicle, no non-polar part of the phospholipid has any contact with the water solution.

Because of their non-polar portions, phospholipids typically are water-insoluble and incompatible with many water soluble anionic compounds, such as anionic surfactants. While they can be solubilized in water at low levels by a range of surfactants, this is often not easily accomplished.

Instead, solubilization has been accomplished conventionally using specific solubilizing agents in aqueous alcoholic solutions. For example, U.S. Pat. No. 4,874,553 to Hager et al. discusses methods of rendering phospholipid mixtures water-soluble or water-dispersible by using certain amine compounds as solubilizing agents. U.S. Pat. No. 4,174,296 to Kass describes a method of improving the solubility of phospholipid compounds in water, in particular lecithin compounds, by mixing lecithin with specific single solubilizing agents, including amphoteric and anionic surfactants. These methods require alcohol for cosolubilization. Alcohol solutions have the drawback of disrupting any bilayer formation by altering the solution such that the alcohol functions as a secondary solvent.

Lecithins and other phospholipids have been used in the pharmaceutical industry to formulate carriers for water-insoluble drugs. For instance, in U.S. Pat. No. 5,173,303 to Lau et al., water-insoluble material is encapsulated by vesicles composed of phospholipids such as lecithin. I. Ribosa et al., in "Physico-chemical modifications of liposome structures through interaction with surfactants," Int'l Journal of Cosmetic Science 14:131–149 (1992), also discuss solubilization of phospholipids via the interaction of liposomes with surfactants. Lau and Ribosa, however, investigated only dilute solutions of pure liposomes.

Despite difficulties in solubilization, certain organic phospholipids, such as lecithin, can advantageously give hair and skin a soft, moisturized feel because they have a strong affinity for the hydrophobic surface of the hair and skin. In addition, these phospholipids are toxicologically safe. It would thus be desirable for cosmetic and pharmaceutical applications to provide delivery systems that include such organic phospholipids as a carrier for other lipophilic ingredients, without the need for alcohols and other similar solvents.

In addition to solubilizing lipophilic ingredients such as oils, vitamins, and ceramides in aqueous systems, it would be desirable to solubilize other water-insoluble ingredients, such as unneutralized or partially neutralized polymers, resins, or latexes, in aqueous delivery systems. U.S. Pat. No. 5,391,368 to Gerstein teaches solubilization of a hair-styling polymer in a composition comprising an anionic surfactant and an amphoteric surfactant. According to Gerstein, it is the amphoteric surfactant which dissolves the water-insoluble styling polymer because the polymer is not soluble in the anionic surfactant alone.

Gerstein presents some problems, however. Many hair care and hair setting products are formulated at acidic pH because of a desire for such products to be compatible with the pH of the scalp and hair surface. Gerstein does not disclose a pH at which its system is formulated, but if the Gerstein system is acidified, the polymer will precipitate out of solution. In addition, the Gerstein system does not carry and there is no suggestion that it could carry any additional lipophilic ingredients in its mixture of anionic surfactant, amphoteric surfactant, and styling polymer. Further, Gerstein does not describe the incorporation of its styling polymer into any products other than the disclosed styling shampoo, nor does Gerstein suggest that such incorporation would be possible.

Thus, there remains a need for an aqueous delivery system that can solubilize water-insoluble materials in such a manner that they will not precipitate out of solution upon acidification, where the amount of deposition of water-insoluble material can be controlled, and where the system could carry other ingredients in addition to the water-insoluble ingredient. For example, it would be beneficial to have a system which incorporates water-insoluble materials into compositions containing other ingredients, such as dyeing and permanent wave compositions. The present invention provides a solution to these problems.

SUMMARY OF THE INVENTION

In order to achieve these and other advantages, the present invention is drawn to a composition made up of at least one organic phospholipid capable of forming bilayers in aqueous solution, at least one amphoteric surfactant, at least one nonionic surfactant, and at least one cationic polymer. The nonionic surfactant is present in an amount by weight equal to or greater than the amount of the organic phospholipid.

In another embodiment, the present invention relates to an aqueous delivery system for water-insoluble materials. As defined herein, "water-insoluble" means one which is insoluble in water but which can be solubilized in accordance with the present invention. The delivery (or "carrier") system includes at least one organic phospholipid capable of forming bilayers in aqueous solution, at least one amphoteric surfactant, at least one nonionic surfactant, at least one cationic polymer, at least one water-insoluble ingredient, and an aqueous phase. The nonionic surfactant is present in an amount by weight equal to or greater than the amount of the organic phospholipid. The organic phospholipid, the amphoteric surfactant, and the nonionic surfactant are present in a combined amount sufficient to allow the lipophilic ingredient to be incorporated into the delivery system.

The present invention is also drawn to a method for treating at least one keratinous substance by preparing an aqueous solution comprising at least one organic phospholipid capable of forming bilayers in aqueous solution; at least one amphoteric surfactant; at least one nonionic surfactant present in an amount by weight equal to or greater than the amount of said at least one phospholipid; at least one cationic polymer; and at least one water-insoluble ingredient. The phospholipid and the two surfactants are present in a combined amount sufficient to allow the water-insoluble ingredient to be incorporated into said aqueous solution. The aqueous solution is then applied to the keratinous substance.

Finally, the present invention relates to methods for controlling the deposition of a water-insoluble ingredient on at least one keratinous substance, by preparing an aqueous solution comprising at least one organic phospholipid capable of forming bilayers in aqueous solution; at least one amphoteric surfactant; at least one nonionic surfactant present in an amount by weight equal to or greater than the amount of said at least one phospholipid; and at least one water-insoluble ingredient. The phospholipid and the two surfactants are present in a combined amount sufficient to allow the water-insoluble ingredient to be incorporated into said aqueous solution. In preparing the aqueous solution, the amount of the organic phospholipid, the amount of the nonionic surfactant, or both, are adjusted in order to control the amount of deposition of the water-insoluble ingredient on the keratinous substance. Cationic polymer(s) are optionally included in the aqueous solution, which is then applied to the keratinous substance.

Reference will now be made in detail to the presently preferred embodiment(s) of the invention.

DETAILED DESCRIPTION OF THE PREFERRED EMBODIMENTS

Advantageously, the present invention allows otherwise water-insoluble materials or ingredients to be solubilized in an aqueous solution. No alcohol is required for cosolubilization, and there is no need for liposome preparation. Further, when the water evaporates, the residue left behind includes the Water-insoluble material and/or the phospholipid. Further, the invention allows for control in the amount of material to be deposited.

The composition of the invention is also easy to formulate and can be gentle on the hair, skin, or eyelashes when the surfactants used are mild. Unlike the attempted solubilization of phospholipids in the prior art, the present invention requires the presence of at least one amphoteric surfactant and at least one nonionic surfactant in the concentrated solutions of phospholipid.

The compositions and delivery systems of the present invention can readily deposit the organic phospholipid/water-insoluble substances on the hair, skin, and eyelashes, and, because of their inherent insolubility, can resist being washed off with water. Further, by the presence of the cationic polymer, and/or by adjusting the amount of the organic phospholipid, the nonionic surfactant, or both, the amount of water-insoluble ingredients deposited can be controlled. Accordingly, these compositions and delivery systems can be used in hair shampoos, conditioners, hair dyeing compositions, including oxidative dyes and bleaches, permanent waving compositions, curl relaxing compositions, hair setting compositions, bath and body products, sunscreens, or cosmetics such as mascaras and foundations.

These systems can also be used to deliver active water-insoluble pharmaceutical ingredients, particularly in topical applications. Such systems could further help protect against oxidation and rancidity by protecting sensitive ingredients in pharmaceuticals or foods.

Additionally, the "load" carried by these systems can be quite high, a benefit that inures both to the, user and to the manufacturer in an economic sense. Load is defined as the weight of added hydrophobe (water-insoluble material) divided by the weight of the phospholipid expressed as a percentage. Thus, 1 g of hydrophobe in a composition with 5 g phospholipid is a ⅕ or 20% load. In the art, 50% is considered a high load and can be achieved with certain hydrophobes and surfactant combinations.

Without being bound to a particular theory, the inventors believe that in the composition of the present invention, an organized structure, likely a laminar gel, is formed between the organic phospholipid and the nonionic surfactant and is solubilized by the amphoteric surfactant. The organized structure can incorporate other water-insoluble materials or hydrophobes. In aqueous systems, the structure remains organized, as evidenced by the clarity of the solution, exhibiting a slight Tyndall light scattering effect, and, when concentrated, showing lamellar anisotropic structures under polarized light.

In one embodiment, therefore, the invention is drawn to a composition comprising at least one organic phospholipid capable of forming bilayers in aqueous solution, at least one amphoteric surfactant, at least one nonionic surfactant, and at least one cationic polymer, where the nonionic surfactant is present in an amount by weight equal to or greater than the amount of the phospholipid.

With respect to the ingredients of the inventive composition, the preferred organic phospholipids capable of forming bilayers in aqueous solution are lecithins. Lecithins are mixtures of phospholipids, i.e., of diglycerides of fatty acids linked to an ester of phosphoric acid. Preferably, lecithins are diglycerides of stearic, palmitic, and oleic acids linked to the choline ester of phosphoric acid. Lecithin is usually defined either as pure phosphatidyl cholines or as crude mixtures of phospholipids which include phosphatidyl choline, phosphatidyl serine, phosphatidyl ethanolamine, phosphatidyl inositol, other phospholipids, and a variety of other compounds such as fatty acids, triglycerides, sterols, carbohydrates, and glycolipids.

The lecithin used in the present invention may be present in the form of a liquid, powder, or granules. Lecithins useful in the invention include, but are not limited to, soy lecithin and hydroxylated lecithin. For example, ALCOLEC S is a fluid soy lecithin, ALCOLEC F 100 is a powder soy lecithin, and ALCOLEC Z3 is a hydroxylated lecithin, all of which are available from the American Lecithin Company.

In the present invention, lecithin is preferably used in an amount greater than 0 to about 3% by weight relative to the total weight of the composition, preferably from about 0.05% to about 1% by weight. Since lecithin itself is not a pure raw material and may have free glycerides, glycerin, fatty acids, and soaps, adjustments in this ratio may need to be made, i.e., one source of lecithin may require different ratios of nonionic and amphoteric surfactants than another to achieve maximum clarity of solution. Preferably, the composition of the invention forms a clear solution, though the purpose of the invention is achieved just as effectively with a slightly cloudy solution.

Other than lecithins, another group of phospholipids which may be useful in the present invention are multifunctional biomimetic phospholipids. For example, the following multifunctional biomimetic phospholipids manufactured by Mona Industries may be useful: PHOSPHOLIPID PTC, PHOSPHOLIPID CDM, PHOSPHOLIPID SV, PHOSPHOLIPID GLA, and PHOSPHOLIPID EFA.

The amphoteric surfactants useful in the present invention include, but are, not limited to, betaines, sultaines, hydroxysultaines, alkyl amphodiacetates, alkyl amphodipropionates, and imidazolines, or salts thereof. It is recognized that other fatty acid condensates such as those formed with amino acids, proteins, and the like are suitable. Amphoteric surfactants are typically available for commercial sale in solution form with the active surfactant accounting for approximately 40% of the total solution weight. Cocamphodipropionate is particularly preferred, for example, MIRANOL C2M-SF Conc. (disodium cocamphodipropionate), in its salt-free form, available from Rhône-Poulenc. MIRANOL is sold in solution form with amphoteric surfactants composing approximately 40% of the total solution weight; for example, 10 g of MIRANOL contain about 4 g of amphoteric surfactant. Also preferred is CROSULTAINE C-50 (cocamidopropyl hydroxysultaine), available from Croda. CROSULTAINE is also sold in solution form with the amphoteric surfactant composing approximately 50% of the total solution weight.

The amphoteric surfactants are preferably present in the composition in an amount ranging from greater than 0 to about 3.6% by weight relative to the total weight of the composition. Preferably, the amphoteric surfactants are present in an amount ranging from about 0.06% to about 1.2% by weight. When, as discussed further infra, the composition of the invention is used in a delivery system for a water-insoluble polymer or resin, the amphoteric surfactants are preferably present in the composition in the same range. Other amphoteric surfactants useful in the present invention include disodium a wheatgermimido PEG-2 sulfosuccinate, available under the trade name MACKANATE WGD from McIntyre Group Ltd., which is a solution with amphoteric surfactants composing approximately 39% of the total solution weight, and disodium soyamphodiacetate, available under the trade name MACKAM 2S from McIntyre Group Ltd., which is a solution with amphoteric surfactants composing approximately 34.5% of the total solution weight.

The nonionic surfactants useful in the present invention are preferably formed from a fatty alcohol, a fatty acid, or a glyceride with a $C_8$ to $C_{24}$ carbon chain, preferably a $C_{12}$ to $C_{18}$ carbon chain, more preferably a $C_{16}$ to $C_{18}$ carbon chain, derivatized to yield a Hydrophilic-Lipophilic Balance (HLB) of at least 10. HLB is understood to mean the balance between the size and strength of the hydrophilic group and the size and strength of the lipophilic group of the surfactant. Such derivatives can be polymers such as ethoxylates, propoxylates, polyglucosides, polyglycerins, polylactates, polyglycolates, polysorbates, and others that would be apparent to one of ordinary skill in the art. Such derivatives may also be mixed polymers of the above, such as ethoxylate/propoxylate species, where the total HLB is preferably greater than or equal to 10. Preferably the nonionic surfactants contain ethoxylate in a molar content of from 10–25, more preferably from 10–20 moles.

Nonionic surfactants may be selected from, but are not limited to, the following:

| # of Cs | Name | Trade Name |
|---|---|---|
| C-12 | Laureth-23 | BRIJ 35, available from ICI Surfactants |
| C-16 | Ceteth-10 | BRIJ 56, available from ICI Surfactants |
| C-16 | Ceteth-20 | BRIJ 58, available from ICI Surfactants |
| C-16 | IsoCeteth-20 | ARLASOLVE 200, available from ICI Surfactants |
| C-18 | Steareth-10 | VOLPO S-10, available from Croda Chemicals Ltd. |
| C-18 | Steareth-16 | SOLULAN-16, available from Amerchol Corp. |
| C-18 | Steareth-20 | BRIJ 78, available from ICI Surfactants |
| C-18 | Steareth-25 | SOLULAN-25, available from Amerchol Corp. |
| C-18 = | Oleth-10 | BRIJ 97, available from ICI Surfactants |
| C-18 = | Oleth-20 | VOLPO-20, available from Croda Chemicals Ltd. |

Alkyl polyglucose surfactants sold under the name PLANTAREN, available from Henkel, may also be used. The nonionic surfactant is preferably present in an amount of greater than 0 to about 20% by weight relative to the weight of the whole composition. More preferably, the nonionic surfactant is present in an amount of about 0.2% to about 5% by weight.

Cationic polymers useful in the present invention include, but are not limited to, polyquaternium 4, polyquaternium 6, polyquaternium 7, polyquaternium 10, polyquaternium 11, polyquaternium 16, polyquaternium 22, polyquaternium 28, polyquaternium 32, and guar hydroxypropyltrimonium chloride. Preferred cationic polymers include POLYMER JR-125 and POLYMER JR-400, hydroxyethyl cellulosic polymers (polyquaternium 10) available from AMERCHOL; JAGUAR C13-S, guar hydroxypropyltrimonium chloride, available from Meyhall; and MERQUAT 100, a dimethyl dialkyl ammonium chloride (polyquaternium 6) available from CALGON. The cationic polymer is preferably present in an amount of about 0.1% to about 5.0% relative to the total weight of the inventive composition.

In one preferred embodiment of the composition of the present invention, the organic phospholipid capable of forming bilayers in aqueous solution, the amphoteric surfactant, and the nonionic surfactant are present in the composition such that the nonionic surfactant is present in an amount by weight greater than the amount of phospholipid. In a more preferred embodiment, the amount of phospholipid in the composition is kept fixed while the amounts of the amphoteric and nonionic surfactants are increased. Preferably, the phospholipid, amphoteric surfactant, and nonionic surfactant are present in a combined amount sufficient to allow at least one water-insoluble ingredient to be incorporated into an aqueous solution.

In a still more preferred embodiment, calculating the phospholipid as present at a value of 1, the phospholipid, amphoteric surfactant and nonionic surfactant are preferably present in the composition in a ratio ranging from about 1:0.8:2 and above by weight relative to the whole composition, i.e., where the amounts of the surfactants can be increased independently of each other but the amount of phospholipid stays fixed. (In other words, a ratio of 1:0.8:2 is equal to 10 g of lecithin, 20 g MIRANOL, and 20 g ARLASOLVE.) The ratio is considered to be "above" 1:0.8:2 when the amount of either of the surfactants increases. When the inventive composition is used in a delivery system for a lipophilic material, the composition also includes water, and the ratio preferably ranges from about 1:1.2:2 and above. When the inventive composition is used in a delivery system for a water-insoluble polymer or resin, the ratio is preferably about 1:1.2:3 and above, and more preferably above about 1:1.2:4. The loading capability for hydrophobes carried by the delivery system of the present invention can be increased if the ratio of nonionic surfactant to phospholipid is minimized, with the bilayers still being solubilized, because an excess of nonionic surfactant may disrupt the organized structure.

In one preferred embodiment, the composition of the present invention comprises ALCOLEC S (soy lecithin), MIRANOL C2M-SF Conc. (disodium cocamphodipropionate, an amphoteric surfactant), ARLA-SOLVE 200 (IsoCeteth-20, a nonionic surfactant) in a ratio of 5:15:10 (which is a LAN ratio of 1:1.2:2) when a lipophilic water-insoluble ingredient is employed, and 5:15:20 (which is a LAN ratio of 1:1.2:4) when a water-insoluble polymer, resin, or latex is employed, wherein the ratios are calculated by weight relative to the whole composition. In general, the preferred compositions of the invention contain, in addition to the cationic polymer, a lecithin (L), an amphoteric surfactant (A), and a nonionic surfactant (N), referred to as the "LAN." Although lecithin is particularly preferred, the types of amphoteric and nonionic surfactants may vary.

When used as an ingredient in further formulations, the LAN is compatible and generally gives clear solutions with anionic surfactants such as alkyl sulfates and ethoxylated alkyl sulfates. Other anionic surfactants such as sulfosuccinates may also be used. Typically, LAN compositions can resist storage at 45° C. for three months or more, which would predict that they have a shelf life at room temperature of at least three years.

In another aspect, the present invention relates to an aqueous delivery or carrier system comprising at least one organic phospholipid capable of forming bilayers in aqueous solution, at least one amphoteric surfactant, at least one nonionic surfactant preferably present in an amount greater than or equal to the amount of the phospholipid, at least one cationic polymer, at least one water-insoluble ingredient, and an aqueous phase. The phospholipid, amphoteric surfactant, and nonionic surfactant are present in a combined amount sufficient to allow the water-insoluble ingredient(s) to be incorporated into or solubilized by the aqueous system. The amount sufficient for solubilization may vary depending on the type of composition; for example, shampoo and mascara formulations require a lower concentration of LAN than do conditioner, deep treatment, bleach, permanent wave, dye, and relaxant compositions. The cationic polymer acts to increase the deposition of both the LAN and its carried ingredient on their ultimate destination, preferably the hair, eyelashes, or skin.

Water-insoluble materials or ingredients useful in the compositions or delivery systems of the present invention include, but are not limited to the following:

(1) Lipophilic "ingredients" or "materials" such as silicones, oil-soluble vitamins such as Vitamin F and Vitamin A, sunscreens, ceramides and natural oils: The lipophilic ingredients may be in the form of sunscreens, bacteriostats, moisturizers, colors, topical pharmaceuticals and the like. Preferred lipophilic ingredients include: Vitamin E, Vitamin E Acetate, Vitamin A Palmitate, olive oil, mineral oil, 2-oleamido-1,3-octadecanediol, octylmethoxy cinnamate, octyl salicylate, and silicones such as dimethicone, cyclomethicone, phenyl trimethicone, dimethiconol, dimethicone copolyol, and laurylmethicone copolyol. The lipophilic ingredients will, for example, moisturize or condition the skin, hair, and/or eyelashes and leave behind no oily feel.

(2) Water-insoluble polymers, resins, and latexes which are unneutralized or partially neutralized, wherein the polymers and resins include but are not limited to those containing carboxyl moieties, such as acrylates and other carboxy polymers. Typically, water-insoluble polymers and resins have to be neutralized to about 90% of their carboxyl moieties to make them water soluble for the purpose of formulating products in aqueous solution and for the purpose of making products which have good non-build-up properties, i.e., can be easily washed off the hair after use. However, when used with the compositions of the present invention, little or no neutralization is needed to dissolve these polymers/resins. In part, an unneutralized or partially neutralized water-insoluble polymer or resin is solubilized because it is neutralized by the amphoteric surfactant contained in the presently claimed delivery system, but the amphoteric surfactant acting alone will not solubilize the polymer or resin in water and allow the pH to be acidic. As discussed with reference to the Gerstein patent above, if the polymer or resin is neutralized by the amphoteric surfactant alone, when one attempts to acidify the solution to prepare a hair care composition with acidic pH, as is desirable, the carboxyl moieties of the polymer or resin become unneutralized and precipitation occurs. It is the combination of the organic phospholipid, the amphoteric surfactant, and the nonionic surfactant of the present invention which achieves the solubility of the water-insoluble polymers or resins.

As for latexes, they generally have been used in cosmetics in an unneutralized form since they are used for their milky (insoluble) appearance. In the context of the present invention, however, water-insoluble latexes are neutralized to an alkaline pH and dissolve, producing a clear solution. To the best of the inventors' knowledge, neutralized latexes have not previously been used in cosmetic compositions.

In the case of the non-neutralized or partially-neutralized polymers or resins, where such substances are applied to the hair or skin from an alcoholic or aqueous/alcoholic system, their washability from the hair leaves a great deal to be desired. In contrast, where such polymers or resins are applied in a delivery system of the present invention, the polymers or resins can easily be rinsed off from the hair (no build-up) while providing strong hold for curls, if curls are what is desired.

The following are examples of polymers that can be incorporated into the delivery system of the present invention. The list is not intended to be limiting:

AMPHOMER LV-71 from National Starch (octylacrylamide/acrylates/butylaminoethyl methacrylate copolymer),
OMNIREZ-2000 from ISP (PVM/MA half ethyl ester copolymer),
RESYN 28-2930 from National Starch (Vinyl acetate/crotonates/vinyl neodecanoate copolymer),
LUVIMER 100P from BASF (t-butyl acrylate/ethyl acrylate/methacrylic acid), and
ULTRAHOLD STRONG from BASF (acrylic acid/ethyl acrylate/t-butyl acrylamide).

Unneutralized or partially neutralized water-insoluble latexes have been used as film-formers in various applications. The following are latexes that can be incorporated into the delivery system of the present invention:

AMERHOLD DR-25 from Amerchol (acrylic acid/methacrylic acid/acrylates/methacrylates),
LUVIMER 36D from BASF (ethyl acrylate/t-butyl acrylate/methacrylic acid), and
ACUDYNE 258 from Rohm & Haas (acrylic acid/methacrylic acid/acrylates/methacrylates/hydroxy ester acrylates).

The aqueous phase of the inventive delivery system can contain additional ingredients such as anionic surfactants, organic salts, inorganic salts, proteins, hair dyes, water-soluble polymers, quaternary ammonium compounds, complex and simple carbohydrates, amino acids, preservatives and fragrances.

If the inventive system is to be used in concentrated form, i.e., with about 5% by weight of the organic phospholipid and 1% of added water-insoluble ingredient, the composition preferably has a pH ranging from 4–12 for maximum stability and clarity. The more concentrated the solution, the better the delivery.

If this blend is diluted with water or the blend is used as an ingredient in another composition, then the pH has a broader range, i.e., preferably ranges from 2–12, and a wider variety of additives can be included in the solution. When water is added to a concentrated LAN, it may appear to form a cloudy solution at first if a large amount of water is added at once. The LAN will eventually go into solution, however, and become clear or at least clearer. The time to clear decreases as the LAN ratio increases. Once the organized structure of the LAN forms, the addition of more water does not affect clarity. These dilute blends are still very effective in delivering water-insoluble ingredients. The blends can be freeze-dried to hygroscopic solids that redissolve into water. Encapsulation of such solids so that they do not pick up and retain excess moisture is also contemplated. Such encapsulated solids can have desirable storage properties and would be easy to dissolve into water at various dilutions. Understandably, the need for dilution varies depending on the water-insouble material to be employed.

In another embodiment, the present invention relates to a method for treating at least one keratinous substance by preparing an aqueous solution comprising at least one organic phospholipid capable of forming bilayers in aqueous solution; at least one amphoteric surfactant; at least one nonionic surfactant present in an amount by weight equal to or greater than the amount of said at least one phospholipid; at least one cationic polymer; and at least one water-insoluble ingredient, wherein the phospholipid, amphoteric surfactant, and nonionic surfactant are present in a combined amount sufficient to allow the water-insoluble ingredient to be incorporated into the aqueous solution; and applying the aqueous solution to the keratinous substance. The keratinous substance is preferably hair, skin, or eyelashes. The type of treatment envisioned by the claimed method may include shampooing, conditioning, dyeing, bleaching, permanent waving, relaxing, setting, moisturizing, and making-up the hair, skin, or eyelashes.

Another embodiment of the present invention is drawn to a process for preparing the aqueous system of the present invention. This process comprises: (a) combining the at least one organic phospholipid, amphoteric surfactant, and nonionic surfactant as described above to obtain a mixture, (b) heating the mixture obtained in step (a), and (c) adding an aqueous solution to the heated mixture to obtain the desired carrier system. Water-insoluble ingredients may be added in step (a). The cationic polymer may be added in Step (c) in the aqueous solution. Preferably the carrier system obtained can carry a high load (i.e., 50% is considered a high load) of the organic phospholipid/water-insoluble ingredient. The mixture is preferably heated at a temperature of 65° C. to 85° C., depending on the melting points of the solid surfactants.

More specifically, the preparation of the carrier system of the present invention maybe carried out as follows. Lecithin (L) is dispersed in water. The water-insoluble material is combined with nonionic surfactant(s) (N) at appropriate ratios and added to the lecithin/water dispersion. An amphoteric surfactant (A) is added and the mixture is heated, preferably to a temperature of from 75° C. to 85° C. The combination of these ingredients results in a solution which is clear to slightly hazy and is referred to as the "LAN," which can then be used as a "raw material" to make finished products. The cationic polymer is added in aqueous solution during the formulation of finished products.

Alternatively, lecithin, amphoteric surfactant(s) and nonionic surfactant(s) can be weighed to appropriate ratios and heated to 70° C. with stirring. As Water is then added at the same temperature. Another alternative method of preparation comprises adding the water-insoluble ingredient with mixing after solutions have cooled. This last alternative method helps protect heat-sensitive water-insoluble ingredients.

The resulting compositions may vary from clear to slightly hazy and are infinitely dilutable with water. The slight haze can be overcome by adjusting the ratio of lecithin to the surfactants, adjusting pH, or reducing concentrations of water-insoluble ingredients.

In yet another aspect, the present invention relates to methods for controlling the deposition of a water-insoluble ingredient on at least one keratinous substance by preparing an aqueous solution comprising at least one organic phospholipid capable of forming bilayers in aqueous solution; at least one amphoteric surfactant; at least one nonionic surfactant present in an amount by weight equal to or greater than the amount of said at least one phospholipid; and at least one water-insoluble ingredient. The phospholipid and the two surfactants are present in a combined amount sufficient to allow the water-insoluble ingredient(s) to be incorporated into said aqueous solution. In preparing the aqueous solution, the amount of the organic phospholipid, the amount of the nonionic surfactant, or both, are adjusted in order to control the amount of deposition of the water-insoluble ingredient on the keratinous substance. Cationic polymer(s) are optionally included in the aqueous solution, which is then applied to the keratinous substance. While, as discussed supra, addition of cationic polymer(s) into this system increases the deposition of the water-insoluble ingredient(s), the deposition can also be effectively controlled by varying the quantities of L, N, or both in the LAN system, with or without the cationic polymer.

By varying the amount of the nonionic surfactant component in the LAN/water-insoluble ingredient system, the amount of the water-insoluble ingredient deposited on hair can be controlled. Since, as discussed above, the nonionic surfactant is necessary to incorporate the water-insoluble ingredient(s) into the LAN system, a high quantity of nonionic surfactant in a LAN solution results in the water-insoluble ingredient(s) having a higher tendency to stay in the LAN solution. In other words, the less nonionic surfactant present in the LAN solution, the easier it is for the water-insoluble ingredient(s) to come out of solution and thus be deposited on, e.g., hair. Therefore, the amount of the LAN/water-insoluble ingredient(s) deposited on hair, skin, or eyelashes can be controlled by the quantity of the nonionic surfactant in the LAN system.

By adjusting the amount of the organic phospholipid, which is preferably lecithin, in the LAN system, the deposition of water-insoluble ingredients on various hair types can be controlled. Since lecithin is lipophilic, it is more attracted to the hydrophobic surface of normal hair (i.e., hair with less damage) than it is to the hydrohilic surface of bleached hair (considered to be "damaged" hair). In other words, higher amounts of lecithin favor the deposition of lipophiles on normal hair and lower lecithin amounts favor deposition on damaged hair.

Accordingly, by adjusting the amounts of both the lecithin and the nonionic surfactant in the LAN system, one can control how much of the water-insoluble ingredient(s) is deposited on which hair types.

As mentioned previously, the composition and delivery system of the present invention can be used as an ingredient itself in, for example, shampoos, conditioners (rinse-off and leave-in), deep treatments for hair, body washes, bath gels, hair dyeing compositions, permanent wave formulations, relaxers, make-up preparations, particularly mascara and foundation, and skin creams or lotions. When the inventive compositions or delivery systems are used as shampoos, at least one anionic surfactant may also be included in the shampoo formulation, as it is a typical shampoo ingredient.

With respect to hair products, the system of the present invention can be used to formulate hair products, e.g., for normal hair, color-treated hair, dry hair, fine hair, and damaged hair. For each type of hair, the LAN can be used to create a regimen comprising shampoo, conditioner, and deep treatment, (i.e., deep conditioner). Additional nonionic, amphoteric, and also anionic surfactants can be added to the LAN. In general, the concentration of the LAN is increased within each regimen from shampoo to conditioner to deep treatment. Thus, the deep treatment formulations have the most concentrated hydrophobe-carrying LAN.

The LAN systems of the invention can be further associated, in the hair products described above, with proteins including hydrolyzed soy protein, lauryldimonium hydrolyzed soy protein (cationic Soya protein) and wheat amino acids. The proteins could also include corn, wheat, milk, or silk proteins, collagens, keratins, or others. Furthermore, taurine and arginine hydrochloride may be associated therein to maximize protein binding to the hair. Cationic proteins or proteins in general may be stabilizers for the LAN and, like the cationic polymers discussed above, enhance its delivery by changing the charge on the surface of the LAN structure. The skin and the hair attract cationic ingredients, and proteins are generally substantive to these tissues.

In conditioning emulsions, nonionic emulsifiers such as glyceryl stearate and PEG-100 stearate can be used, and the LAN may be treated as a water-insoluble, particularly a lipophilic, ingredient itself.

Other ingredients in the LAN hair care compositions may include isoparaffins, sodium chloride, propylene glycol, preservatives such as phenoxyethanol, methylparaben, ethylparaben, and propylparaben, pH adjusters such as phosphoric acid, humectants such as trehalose, and emollients such as octyldodecanol. Many other examples of materials from the classes listed above would be readily known to one of ordinary skill in the art.

Further, shampoos, conditioners, and deep treatments within the scope of the present invention may be used on hair which has been treated, e.g., with color (dye or bleach) or chemicals (permanent wave or straightening), or which is dry or fine and show significant substantivity for the hair.

The invention will be further clarified by the following examples, which are intended to be illustrative of the invention, but not limiting thereof.

EXAMPLES

Example 1

LAN as Co-precipitant in Shampoo

Cationic species are known to form a complex with anionic surfactants wherein the resulting solids precipitate out of the solution upon addition of water. When a LAN composition was incorporated in a cationic polymer-anionic surfactant system (e.g., an anionic shampoo containing cationic conditioning agents), it also precipitated along with the cationic-anionic complex. As shown in Table 1, a clear shampoo containing LAN, a cationic polymer (POLYMER JR 125), and an anionic surfactant (SLES) was prepared and was found to give a precipitate upon dilution with water. The precipitate was obtained by centrifugation; the amount of the solid was determined gravimetrically and its phosphorus content (evidence of lecithin) was analyzed by atomic absorption. A second shampoo was prepared which contained the same ingredients but no LAN. Analysis of the two shampoos showed that when LAN was present, more precipitate with a higher phosphorus content was obtained, an indication that the precipitate contains a high amount of LAN. See results in Table 1 below.

TABLE 1

|  | SOLUTION 1 | SOLUTION 2 |
| --- | --- | --- |
| POLYMER JR-125 | 0.15 g | 0.15 g |
| SLES (anionic surfactant) | 1.5 g | 1.5 g |
| LAN* (1:1.2:4) | 3.0 g | — |
| Water | 13.65 g | 16.65 g |
| Precipitate | 0.30 g | 0.05 g |
| Phosphorus Content | 0.36% | trace |

*LAN was composed of ALCOLEC S (L), MIRANOL C2M-SF Conc. (where 40% of total solution weight was active A), and ARLASOLVE 200 (N).

Example 2

Increasing the Deposition of LAN/Water-Insoluble Ingredients on Hair

In Example 1, it was shown that LAN precipitated in an anionic system containing cationic polymers. In a similar system additionally containing a water-insoluble ingredient, the presence of the cationic polymers increased the deposition of LAN and its carried ingredients on hair. Example 1 was repeated with LAN (1:1.2:4) containing 0.5% silicone (Dow Corning 200) as the water-insoluble ingredient. The results (see Table 2 below) showed that silicone was also precipitated along with the LAN/SLES/Polymer JR complex:

TABLE 2

|  | SOLUTION 1 | SOLUTION 2 |
| --- | --- | --- |
| POLYMER JR-125 | 0.15 g | 0.15 g |
| SLES (anionic surfactant) | 1.5 g | 1.5 g |
| LAN* (1:1.2:4)/Silicone | 3.0 g | — |
| Water | 13.65 g | 16.65 g |
| Precipitate | 0.30 g | 0.08 g |
| Silicone (Si) Content | 2.90% | 0.70% |

*LAN was composed of ALCOLEC S (L), MIRANOL C2M-SF Conc. (where 40% of total solution weight was active A), and ARLASOLVE 200 (N).

The above results show that when a LAN composition containing a cationic polymer and carrying a water-insoluble ingredient is prepared as a shampoo, upon rinsing, the lecithin along with the water-insoluble ingredient (in this example, silicone) will precipitate and deposit on hair.

Example 3

Increasing the Deposit of LAN/Water Insoluble Ingredients in the Presence of Cationic Polymer in Shampoo Systems The following shampoos were adopted from Example 2 of U.S. Pat. No. 3,996,146, to which 10 g of a solution containing LAN (1:1.2:4) (the components were 5 g ALCOLEC S:15 g MIRANOL C2M-SF Conc.:20 g ARLASOLVE 200 ), 1 g Octylmethoxy Cinnamate (OMC, a sunscreen), and 59 g water was added:

TABLE 3

|  | Sulfosuccinate | Betaine | Nonylphenol ethoxylate | MERQUAT 100 | LAN/OMC | Water |
|---|---|---|---|---|---|---|
| Shampoo 1 | 35 g | 16 g | 5 g | 0.2 g | — | 43.8 g |
| Shampoo 2 | 35 g | 16 g | 5 g | 0.2 g | 10 g | 33.8 g |
| Shampoo 3 | 35 g | 16 g | 5 g | — | 10 g | 34.0 g |

Shampoo 1 was a control that contained the cationic polymer (MERQUAT 100) but no LAN/OMC. Shampoo 2 contained the cationic polymer and the LAN/OMC. Shampoo 3 contained only the LAN/OMC and not the cationic polymer. Hair was treated with the above shampoos for 3 minutes, then rinsed for 30 seconds. The hair was shampooed and rinsed an additional 4 times (total shampoo: 5 times). The hair was extracted with alcohol and the extracted OMC determined by UV-Vis. The amount of OMC found on the tested hair, after adjusting from the control, was found to be 3 times higher when the cationic polymer was present. See Table 4 below:

TABLE 4

| TREATMENT | $\mu$g OMC/g Hair |
|---|---|
| Shampoo 2: containing LAN/OMC and MERQUAT 100 | 29.40 |
| Shampoo 3: containing LAN/OMC and no MERQUAT 100 | 9.27 |

Example 4

Increasing the Deposit of LAN/Water Insoluble Ingredients in the Presence of Cationic Polymer in Aqueous Systems Three solutions containing aqueous non-shampoo systems were prepared.

The acqueous systems further contained LAN/OMC as defined in Example 3 and the cationic polymer (POLYMER JR 400). Solution 1 contained the cationic polymer and the LAN/OMC complex as defined in Example 3. Solution 2 contained the LAN/OMC only. Solution 3 contained LAN only. The composition of each solution is shown below in Table 5.

TABLE 5

|  | SOLUTION 1 | SOLUTION 2 | SOLUTION 3 |
|---|---|---|---|
| POLYMER JR-400 | 0.5 | — | — |
| LAN/OMC | 10 | 10 | — |
| LAN | — | — | 10 |
| Water | 89.5 | 90 | 90 |

Solution 3, containing LAN without the sunscreen or the cationic polymer, acted as a control.

Following the same treatment and measurement described above in Example 3, it was found that the amount of sunscreen deposited on the hair, after adjusting for the control, increased in the presence of the cationic polymer. See Table 6:

TABLE 6

| TREATMENT | $\mu$g OMC/g Hair |
|---|---|
| Solution 1: containing LAN/OMC and POLYMER JR-400 | 88.46 |
| Solution 2: containing LAN/OMC and no POLYMER JR-400 | 76.85 |

Example 5

Controlling Deposit of LAN/Water-Insoluble Ingredients on Hair by Adjusting the Amount of L and/or N By adjusting the quantity of the L and the N in the LAN, one can control the deposit of the water-insoluble ingredients in LAN systems in two ways: the quantity of lipophilic ingredients deposited on hair and also the deposition as it is related to varying hair types.

A. Regulation of the Amount of Deposited Water-Insoluble Ingredients Using the N Component The following LAN solutions (low N and high N) containing 0.1% Octyl Methoxy Cinnamate (OMC) as the water-insoluble ingredient were prepared:

TABLE 7

|  | ALCOLEC | MIRANOL | ARLASOLVE | OMC | WATER |
|---|---|---|---|---|---|
| SOLUTION 1 | 0.05 | 0.15 | 0.20 | 0.1 | 99.05 |
| SOLUTION 2 | 0.05 | 0.15 | 0.40 | 0.1 | 98.85 |

Two types of hair (normal brown and bleached) were treated with these solutions for 1 minute at room temperature then rinsed with warm water for 30 seconds and blow-dried. The treatment was repeated for a total of 5 times. The hair was extracted with alcohol and the amount of extracted OMC determined by UV-Vis. As shown below, the amounts of OMC found on both hair, types were controlled by the quantity of N in the LAN system—lower deposit at high N and higher deposit at low N.

TABLE 8

| Treatment | μg OMC/g Hair |
|---|---|
| Normal Hair | |
| Solution 1 (low N) | 90.96 |
| Solution 2 (high N) | 83.99 |
| Bleached Hair | |
| Solution 1 (low N) | 106.05 |
| Solution 2 (high N) | 67.73 |

As discussed above, addition of cationic species into this system increases the deposition of the lipophilic ingredients on hair, this deposition is still effectively controlled by the quantity of N in the LAN system. Hair was treated as described above with the following solutions:

TABLE 9

| | ALCOLEC | MIRANOL | ARLASOLVE | OMC | POLYMER JR-400 | WATER |
|---|---|---|---|---|---|---|
| SOLUTION A | 0.05 | 0.15 | 0.20 | 0.1 | 0.1 | 99.4 |
| SOLUTION B | 0.05 | 0.15 | 0.40 | 0.1 | 0.1 | 98.2 |
| SOLUTION C | 0.05 | 0.15 | 0.20 | 0.1 | — | 99.5 |
| SOLUTION D | 0.05 | 0.15 | 0.40 | 0.1 | — | 99.3 |

After treatment, the amount of OMC extracted from hair treated with solutions containing low N and the cationic polymer increased in the presence of the cationic polymer. Thus, the deposition is controlled by the N in both cases, as shown below in Table 10:

TABLE 10

| Treatment | μg OMC/g Hair |
|---|---|
| Normal Hair | |
| Solution A (low N - with cationic polymer) | 104.89 |
| Solution B (high N - with cationic polymer) | 89.79 |
| Solution C (low N - w/o cationic polymer) | 94.44 |
| Solution D (high N - w/o cationic polymer) | 86.64 |
| Bleached Hair | |
| Solution A (low N - with cationic polymer) | 123.48 |
| Solution B (high N - with cationic polymer) | 96.77 |
| Solution C (low N - w/o cationic polymer) | 117.67 |
| Solution D (high N - w/o cationic polymer) | 77.02 |

B. Regulation of Deposition on Different Hair Types Using L Component

The following shampoos were adopted from Example 2 of U.S. Pat. No. 3,996,146, to which a solution containing LAN/0.1% OMC was added:

TABLE 11

| | Shampoo A | Shampoo B |
|---|---|---|
| Sulfosuccinate | 35.0 | 35.0 |
| Betaine | 16.0 | 16.0 |
| Nonylphenol ethoxylate | 5.0 | 5.0 |
| MERQUAT 100 | 0.2 | 0.2 |
| ALCOLEC | 0.5 | 0.05 |
| MIRANOL | 0.15 | 0.15 |
| ARLASOLVE | 0.2 | 0.2 |

TABLE 11-continued

| | Shampoo A | Shampoo B |
|---|---|---|
| OMC | 0.1 | 0.1 |
| Water | 42.85 | 43.3 |

Two types of hair (normal brown and bleached) were treated with these shampoos for 1 minute at room temperature, then rinsed with warm water for 30 seconds and blow dried. The treatment was repeated for a total of 5 times. The hair was extracted with alcohol and the amount of extracted OMC determined by UV-Vis. As shown in Table 12, the amounts of OMC found on both hair types were controlled by the quantity of the lecithin in the LAN system—low L increased the deposition of lipophilic ingredients on damaged hair and high L increased the deposition on normal hair.

TABLE 12

| Treatment | μg OMC/g Hair |
|---|---|
| Normal Hair | |
| Shampoo A (high L) | 26.26 |
| Shampoo B (low L) | 24.4 |
| Bleached Hair | |
| Shampoo A (high L) | 0.72 |
| Shampoo B (low L) | 0.95 |

C. Regulation of the Deposition Using Both L and N Components

To depict this concept, the inventors devised the following scheme which is based on three observations coming from the above results:

Low N increases the deposition compared to high N
High L favors deposition on normal hair, low L favors deposition on damaged hair
N controls deposition more efficiently than L.

| High Deposition | --------------------------------> | | Low Deposition |
|---|---|---|---|
| Virgin Hair | | | |
| High L–Low N | Low L–Low N | High L–High N | Low L–High N |
| Damaged Hair | | | |
| Low L–Low N | High L–Low N | Low L–High N | High L–High N |

The ensuing experiment illustrates the feasibility of this controlled deposition scheme. The following shampoos were adopted from Example 2 of U.S. Pat. No. 3,996,146, to which absolution containing LAN/0.1% OMC was added:

TABLE 13

|  | Shampoo A (High L–Low N) | Shampoo B (Low L–Low N) | Shampoo C (Low L–High N) | Shampoo D (High L–High N) |
|---|---|---|---|---|
| Sulfosuccinate | 35.0 | 35.0 | 35.0 | 35.0 |
| Betaine | 16.0 | 16.0 | 16.0 | 16.0 |
| Nonylphenol ethoxylate | 5.0 | 5.0 | 5.0 | 5.0 |
| MERQUAT 100 | 0.2 | 0.2 | 0.2 | 0.2 |
| ALCOLEC | 0.5 | 0.05 | 0.05 | 0.5 |
| MIRANOL | 1.5 | 1.5 | 1.5 | 1.5 |
| ARLASOLVE | 2.0 | 2.0 | 4.0 | 4.0 |
| OMC | 0.1 | 0.1 | 0.1 | 0.1 |
| Water | 39.70 | 40.15 | 38.15 | 37.70 |

Two types of hair (normal brown and bleached) were treated with these shampoos for 1 minute at room temperature, then rinsed with warm water for 30 seconds and blow-dried. The treatment was repeated for a total of 5 times. The hair was extracted with alcohol and the amount of extracted OMC determined by UV-Vis. The results are shown below in Table 14.

TABLE 14

| High Deposition | ----------------------------------------> | | Low Deposition |
|---|---|---|---|
| Shampoo A (High L–Low N) | Shampoo B (Low L–Low N) | Shampoo C (Low L–High N) | Shampoo D (High L–High N) |
| Quantity OMC deposited on Virgin Hair ($\mu$g OMC/g hair) | | | |
| 26.26 | 24.4 | 6.87 | 10.35 |
| Quantity OMC deposited on Damaged Hair ($\mu$g OMC/g hair) | | | |
| 0.72 | 0.95 | 0 | 0 |

These data show that the LAN system can be used to regulate the amount of water-insoluble ingredients deposited on hair of any specific type.

It will be apparent to those skilled in the art that various modifications and variations can be made in the composition, delivery systems, and methods of the invention without departing from the spirit or scope of the invention. Thus, it is intended that the present invention cover the modifications and variations of this invention provided that they come within the scope of the appended claims and their equivalents.

What is claimed is:

1. A composition comprising:
   at least one phospholipid capable of forming bilayers in aqueous solution;
   at least one amphoteric surfactant;
   at least one nonionic surfactant present in an amount by weight equal to or greater than the amount of said at least one phospholipid; and
   at least one cationic polymer.

2. A compositions according to claim 1, wherein said composition further comprises at least one anionic surfactant.

3. A composition according to claim 1, wherein said composition further comprises water.

4. A composition according to claim 1, wherein said at least one nonionic surfactant is present in an amount by weight greater than the amount of said at least one phospholipid.

5. A composition according to claim 1, wherein said at least one amphoteric surfactant is present in an amount by weight greater than the amount of said at least one phospholipid.

6. A composition according to claim 1, wherein said at least one phospholipid capable of forming bilayers in aqueous solution is a lecithin.

7. A composition according to claim 1, wherein said at least one phospholipid, said at least one amphoteric surfactant, and said at least one nonionic surfactant are present in a combined amount sufficient to allow at least one water-insoluble ingredient to be incorporated into an aqueous solution.

8. A composition according to claim 7, wherein said at least one water-insoluble ingredient is selected from unneutralized and partially neutralized water-insoluble polymers, resins, and latexes.

9. A composition according to claim 6, wherein said water-insoluble polymers, resins, and latexes contain at least one carboxyl moiety.

10. A composition according to claim 7, wherein said at least one water-insoluble ingredient is a lipophilic ingredient.

11. A composition according to claim 10, wherein said lipophilic ingredient is a silicone, oil-soluble vitamin, ceramide, natural oil, a sunscreen, or a mixture thereof.

12. A composition according to claim 11, wherein said at least one amphoteric surfactant is selected from betaines, sultaines, hydroxysultaines, alkyl amphodiacetates, alkyl amphodipropionates, imidazolines, and salts thereof.

13. A composition according to claim 12, wherein said at least one amphoteric surfactant is cocamphodipropionate or cocamidopropyl hydroxysultaine.

14. A composition according to claim 1, wherein said at least one nonionic surfactant is formed from at least a $C_8$ to $C_{24}$ fatty alcohol, a $C_8$ to $C_{24}$ fatty acid, or a $C_8$ to $C_{24}$ glyceride.

15. A composition according to claim 1, wherein said at least one nonionic surfactant has an HLB of at least 10.

16. A composition according to claim 1, wherein said at least one cationic polymer is polyquaternium 4, polyquaternium 6, polyquaternium 7, polyquaternium 10, polyquaternium 11, polyquaternium 16, polyquaternium 22, 28, polyquaternium 32, or guar hydroxypropyltrimonium chloride.

17. A composition according to claim 1, wherein said at least one cationic polymer is present in an amount of about 0.1% to about 5.0% by weight relative to the total weight of the composition.

18. A composition according to claim 1, wherein said at least one phospholipid, said at least one amphoteric surfactant, and said at least one nonionic surfactant are present in a ratio of 1:0.8:2 and above by weight.

19. A composition to claim 8, wherein said at least one phospholipid, said at least one amphoteric surfactant, and said at least one nonionic surfactant are present in a ratio of 1:1.2:3 and above by weight.

20. A composition according to claim 19, wherein said at least one phospholipid, said at least one amphoteric surfactant, and said at least one nonionic surfactant are present in a ratio of 1:1.2:4 and above by weight.

21. A composition according to claim 11, wherein said at least one phospholipid, said at least one amphoteric surfactant, and said at least one nonionic surfactant are present in a ratio of 1:1.2:2 and above by weight.

22. A method of delivering at least one water insoluble ingredient to at least one keratinous substance comprising:
preparing an aqueous solution comprising at least one phospholipid capable of forming bilayers in aqueous solution; at least one amphoteric surfactant; at least one nonionic surfactant present in an amount by weight equal to or greater than the amount of said at least one phospholipid; at least one cationic polymer; and said at least one water-insoluble ingredient, wherein said at least one phospholipid, said at least one amphoteric surfactant, and said at least one nonionic surfactant are present in a combined amount sufficient to allow said water-insoluble ingredient to be incorporated into said aqueous solution; and
applying said aqueous solution to said at least one keratinous substance.

23. A method according to claim 22, wherein said at least one keratinous substance is selected from hair, skin, and eyelashes.

24. A method according to claim 22, wherein said applying further comprises shampooing, conditioning, dyeing, bleaching, permanent waving, relaxing, setting, moisturizing, or making-up said at least one keratinous substance.

25. A delivery system for water-insoluble ingredients comprising:
at least one phospholipid capable of forming bilayers in aqueous solution;
at least one amphoteric surfactant;
at least one nonionic surfactant present in an amount by weight equal to or greater than the amount of said at least one phospholipid;
at least one cationic polymer;
at least one water-insoluble ingredient; and
an aqueous phase,
wherein said at least one phospholipid, said at least one amphoteric surfactant, and said at least one nonionic surfactant are present in a combined amount sufficient to allow said at least one water-insoluble ingredient to be incorporated into said system.

26. A delivery system according to claim 25, wherein said aqueous phase further comprises additional ingredients selected from anionic surfactants, organic salts, inorganic salts, proteins, hair dyes, water-soluble polymers, amino acids, quaternary ammonium compounds, complex and simple carbohydrates, preservatives, and fragrances.

27. A delivery system according to claim 25, wherein said at least one water-insoluble ingredient is selected from unneutralized and partially neutralized water-insoluble polymers, resins, and latexes.

28. A delivery system according to claim 27, wherein said water-insoluble polymers, resins, and latexes contain at least one carboxyl moiety.

29. A delivery system according to claim 25, wherein said at least one water-insoluble ingredient is a lipophilic ingredient.

30. A delivery system according to claim 29, wherein said lipophilic ingredient is a silicone, oil-soluble vitamin, ceramide, natural oil, a sunscreen or a mixture thereof.

31. A delivery system according to claim 25, wherein said at least one phospholipid capable of forming bilayers in aqueous solution is a lecithin.

32. A delivery system according to claim 25, wherein said at least one amphoteric surfactant is selected from betaines, sultaines, hydroxysultaines, alkyl amphodiacetates, alkyl amphodipropionates, imidazolines, and salts thereof.

33. A delivery system according to claim 32, wherein said at least one amphoteric surfactant is cocamphodipropionate or cocamidopropyl hydroxysultaine.

34. A delivery system according to claim 25, herein said at least one nonionic surfactant is formed from a $C_8$ to $C_{24}$ fatty alcohol, a $C_8$ to $C_{24}$ fatty acid, or a $C_8$ to $C_{24}$ glyceride.

35. A delivery system according to claim 25, wherein said at least one cationic polymer is polyquaternium 4, polyquaternium 6, polyquaternium 7, polyquaternium 10, polyquaternium 11, polyquaternium 16, polyquaternium 22, polyquaternium 28, polyquaternium 32, or guar hydroxypropyltrimonium chloride.

36. A delivery system according to claim 25, wherein said at least one phospholipid is present in an amount of greater than 0 to about 3% by weight relative to the total weight of said delivery system.

37. A delivery system according to claim 25, wherein said at least one amphoteric surfactant is present in an amount of greater than 0 to about 9% by weight relative to the total weight of said delivery system.

38. A delivery system according to claim 25, wherein said at least one nonionic surfactant is present in an amount of greater than 0 to about 20% by weight relative to the total weight of said delivery system.

39. A delivery system according to claim 25, wherein said at least one phospholipid, said at least one amphoteric surfactant, and said at least one nonionic surfactant are present in a ratio of 1:0.8:2 and above by weight.

40. A delivery system according to claim 39, wherein said at least one phospholipid, said at least one amphoteric surfactant, and said at least one nonionic surfactant are present in a ratio of 1:1.2:3 and above by weight.

41. A delivery system according to claim 40, wherein said at least one phospholipid, said at least one amphoteric surfactant, and said at least one nonionic surfactant are present in a ratio of 1:1.2:4 and above by weight.

42. A delivery system according to claim 29, wherein said at least one phospholipid, said at least one amphoteric surfactant, and said at least one nonionic surfactant are present in a ratio of 1:1.2:2 and above by weight.

43. A delivery system according to claim 25, wherein said at least one phospholipid is a lecithin, said at least one amphoteric surfactant is disodium cocamphodipropionate, said at least one nonionic surfactant is selected from PPG-5-Ceteth-20 and Oleth-10 and said cationic polymer is selected form polyquaternium 10, guar hydroxypropyltrimonium chloride, and polyquaternium 6.

44. A delivery system according to claim 25, wherein said system is in the form of a shampoo, a conditioner, a deep treatment for hair, a body wash, a bath gel, a bath oil, a hair dyeing composition, a permanent wave formulation, a make-up composition, a skin cream, or a lotion.

45. A method for controlling the deposition of a water-insoluble ingredient on at least one keratinous substance, said method comprising:

preparing an aqueous solution comprising at least one phospholipid capable of forming bilayers in aqueous solution; at least one amphoteric surfactant; at least one nonionic surfactant present in an amount by weight equal to or greater than the amount of said at least one phospholipid, said at least one water-insoluble ingredient, wherein said at least one phospholipid, said at least one amphoteric surfactant; and said at least one nonionic surfactant are present in a combined amount sufficient to allow said water-insoluble ingredient to be incorporated into said aqueous solution;

applying said aqueous solution to said at least one keratinous substance; and controlling the amount of deposition of said water-insoluble ingredient on said at least one keratinous substance by adjusting the amount of said at least one phospholipid in said aqueous solution.

46. A method according to claim 45, wherein said aqueous solution further comprises at least one cationic polymer.

47. A method for controlling the deposition of a water-insoluble ingredient on at least one keratinous substance, said method comprising:

preparing an aqueous solution comprising at least one phospholipid capable of forming bilayers in aqueous solution; at least one amphoteric surfactant; at least one nonionic surfactant present in an amount by weight equal to or greater than the amount of said at least one phospholipid; and at least one water-insoluble ingredient, wherein said at least one phospholipid, said at least one amphoteric surfactant, and said at least one nonionic surfactant are present in a combined amount sufficient to allow said water-insoluble ingredient to be incorporated into said aqueous solution;

applying said aqueous solution to said at least one keratinous substance; and controlling the amount of deposition of said water-insoluble ingredient on said at least one keratinous substance by adjusting the amount of said at least one nonionic surfactant in said aqueous solution.

48. A method according to claim 47, wherein said aqueous solution further comprises at least one cationic polymer.

49. A method for controlling the deposition of a water-insoluble ingredient on at least one keratinous substance, said method comprising:

preparing an aqueous solution comprising at least one phospholipid capable of forming bilayers in aqueous solution; at least one-amphoteric surfactant; at least one nonionic surfactant present in an amount by weight equal to or greater than the amount of said at least one phospholipid; and at least one water-insoluble ingredient, wherein said at least one phospholipid, said at least one amphoteric surfactant, and said at least one nonionic surfactant are present in a combined amount sufficient to allow said water-insoluble ingredient to be incorporated into said aqueous solution;

applying said aqueous solution to said at least one keratinous substance; and controlling the amount of deposition of said water-insoluble ingredient on said at least one keratinous substance by adjusting the amount of said at least one phospholipid and the amount of said at least one nonionic surfactant in said aqueous solution.

50. A method according to claim 49, wherein said aqueous solution further comprises at least one cationic polymer.

* * * * *

UNITED STATES PATENT AND TRADEMARK OFFICE
CERTIFICATE OF CORRECTION

PATENT NO. : 6,524,614 B2
DATED : February 25, 2003
INVENTOR(S) : David W. Cannell et al.

It is certified that error appears in the above-identified patent and that said Letters Patent is hereby corrected as shown below:

<u>Title page,</u>
Item [75], Inventors, "Edison, NY" should read -- Edison, NJ --.

<u>Column 17,</u>
Line 56, "compositions" should read -- composition --.

<u>Column 18,</u>
Line 43, "claim 6," should read -- claim 8, --.
Line 51, "claim 11," should read -- claim 1, --.
Line 65, "28," should read -- polyquaternium 28, --.

<u>Column 19,</u>
Line 9, "composition to" should read -- composition according to --.

<u>Column 20,</u>
Line 20, "herein" should read -- wherein --.
Line 57, "Oleth-10 and" should read -- Oleth-10, and --.
Line 58, "form" should read -- from --.

Signed and Sealed this

Twenty-second Day of April, 2003

JAMES E. ROGAN
*Director of the United States Patent and Trademark Office*